(12) United States Patent
Abbas

(10) Patent No.: US 10,006,906 B2
(45) Date of Patent: Jun. 26, 2018

(54) DETECTION ASSAYS AND METHODS

(71) Applicant: REGENTS OF THE UNIVERSITY OF MINNESOTA, Minneapolis, MN (US)

(72) Inventor: Abdennour Abbas, St. Paul, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 30 days.

(21) Appl. No.: 15/055,217

(22) Filed: Feb. 26, 2016

(65) Prior Publication Data

US 2016/0252502 A1    Sep. 1, 2016

Related U.S. Application Data

(60) Provisional application No. 62/121,863, filed on Feb. 27, 2015.

(51) Int. Cl.
G01N 33/53 (2006.01)
G01N 33/543 (2006.01)
G01N 33/52 (2006.01)
G01N 33/58 (2006.01)

(52) U.S. Cl.
CPC ....... *G01N 33/54306* (2013.01); *G01N 33/52* (2013.01); *G01N 33/5308* (2013.01); *G01N 33/586* (2013.01); *G01N 33/587* (2013.01); *G01N 2469/00* (2013.01)

(58) Field of Classification Search
None
See application file for complete search history.

(56) References Cited

U.S. PATENT DOCUMENTS

| | | |
|---|---|---|
| 2004/0180380 A1 | 9/2004 | Lee |
| 2008/0199851 A1 | 8/2008 | Egan |
| 2009/0280504 A1 | 11/2009 | Lu |
| 2010/0317020 A1 | 12/2010 | Roscoe |
| 2012/0202218 A1 | 8/2012 | Liedberg |
| 2012/0276523 A1 | 11/2012 | Haselton |
| 2013/0203073 A1 | 8/2013 | Mager |

FOREIGN PATENT DOCUMENTS

WO    WO 2008/086054 A2    7/2008

OTHER PUBLICATIONS

Application No. PCT/US2016/019772, filed Feb. 26, 2016; International Preliminary Report on Patentability dated Sep. 8, 2017; 14 pages.
Abbas, "Molecular linker-mediated self-assembly of gold nanoparticles: understanding and controlling the dynamics" Jan. 2013 *Langmuir* 29(1):56-64. doi: 10.1021/1a303368q. Epub 2012.
(Continued)

*Primary Examiner* — Changhwa J Cheu
(74) *Attorney, Agent, or Firm* — Mueting, Raasch & Gebhardt, PA

(57) ABSTRACT

This disclosure describes assay methods and kits for detecting a target. The methods and kits can be used to detect a target that is present in a sample at low concentration because the methods and kits amplify the signal indicating the presence of target in the sample. Generally, the methods and kits involve nanoparticle aggregation as a detectable signal that is enhanced by a trigger released from a vesicular compartment when the target is bound to a capture agent.

6 Claims, 11 Drawing Sheets

(56) References Cited

OTHER PUBLICATIONS

Abbas, "Freezing the self-assembly process of gold nanocrystals" Dec. 2011 Chem. Commun. 48(11):1677-1679.
Acres, "Mechanisms of Aggregation of Cysteine Functionalized Gold Nanoparticles" Apr. 2014 J. Phys. Chem. 118(19):10481-10487.
Aili, "Hybrid nanoparticle-liposome detection of phospholipase activity" Apr. 2011 Nano Letters, 11(4):1401-5. doi: 10.1021/nl1024062. Epub Aug. 26, 2010.
An, "Preparation of monodisperse and size-controlled poly(ethylene glycol) hydrogel nanoparticles using liposome templates" Mar 2009 J. Colloid Interface Sci., 331(1):98-103.
Anker, "Biosensing with plasmonic nanosensors" 2008 Nat. Mater. 7:442-453.
Bui, "Single-Digit Pathogen and Attomolar Detection with the Naked Eye Using Liposome-Amplified Plasmonic Immunoassay" Aug. 2015, Nano letters, 15(9):6239-6246.
Chen, "Plasmon-Enhanced Colorimetric ELISA with Single Molecule Sensitivity" Mar. 2011 Nano Letters, 11(4):1826-1830.
Chen, "Plasmon-enhanced enzyme-linked immunosorbent assay on large arrays of individual particles made by electron beam lithography" 2013 ACS Nano., 7:8824-8832. doi: 10.1021/nn403287a.
Chen, "Synthesis of fluorescent gold nanodot-liposome hybrids for detection of phospholipase C and its inhibitor" Sep. 2013 Anal. Chem., 85(18):8834.
Cho, "Nano/micro and spectroscopic approaches to food pathogen detection" May 2014 J. Annu. Rev. Anal. Chem. 7:65-88.
De La Rica, "Plasmonic ELISA for the detection of analytes at ultralow concentrations with the naked eye" Sep. 2013 Nat Protoc., 8(9):1759-64. doi:10.1038/nprot.2013.085. Epub Aug. 22, 2013.
De La Rica, "Plasmonic ELISA for the ultrasensitive detection of disease biomarkers with the naked eye" Jun. 2012 Nature Nanotechnology,7:821-824. doi:10.1038/nnano.2012.186.
Enustun, "Coagulation of Colloidal Gold" Nov. 1963 J. Am. Chem. Soc., 85(21):3317.
Etzioni, "The case for early detection" Apr. 2003 Nat. Rev. Cancer 3(4):243-252.
Gandra, "Plasmonic Planet—Satellite Analogues: Hierarchical Self-Assembly of Gold Nanostructures" Apr. 2012 Nano Lett. 12(5):2645-2651.
Goldschmidt, "Comparison of an Amplified Enzyme-Linked Immunosorbent Assay with Procedures Based on Molecular Biology for Assessing Human Immunodeficiency Virus Type 1 Viral Load" Jul. 1998 Clinical and diagnostic laboratory immunology, 5(4):513-518.
Gomes, "Stable polymethacrylate nanocapsules from ultraviolet light-induced template radical polymerization of unilamellar liposomes" Aug. 2006 Langmuir, 22(18):7755.
Grabar, "Preparation and Characterization Monolayers" 1995 J. Anal. Chem. 67(4):735-743.
Hu, "Responsive Polymers for Detection and Sensing Applications: Current Status and Future Developments" Sep. 2010 Macromolecules, 43(20):8315.
International Search Report dated May 11, 2016; 18 pages.

Kim, "Large-scale femtoliter droplet array for digital counting of single biomolecules" Aug. 2012 Lab Chip, 12:4986.
Kosaka, "Detection of cancer biomarkers in serum using a hybrid mechanical and optoplasmonic nanosensor" Nov. 2014 J. Nat Nano 9:1047-1053.
Lequin, "Enzyme immunoassay (EIA)/enzyme-linked immunosorbent assay (ELISA)" Dec. 2005 Clin. Chem. 51(12):2415-2418.
Lichtenberg, "Liposomes: Preparation, Characterization, and Preservation" in Methods of Biochemical Analysis, John Wiley & Sons, Inc.: 2006, 337-462.
Liu, "Liposomes in biosensors" Jan. 2013 Analyst, 138(2):391.
Ngo, "Liposome encapsulation of conjugated polyelectrolytes: Toward a liposome beacon" Dec. 2007 J. Am. Chem. Soc. 130(2):457-459.
Pollok, "Modern Techniques for Pathogen Detection" Ed.: Popp Wiley-VCH Verlag GmbH & Co. KGaA: Hoboken, NJ; 2015; 330 pages.
Qu, "Copper-mediated amplification allows readout of immunoassays by the naked eye" Apr. 2011 Angew Chem Int Ed., 50(15):3442-3445.
Rissen, "Single-molecule enzyme-linked immunosorbent assay detects serum proteins at subfemtomolar concentrations" Jun. 2010 Nature Biotechnology, 28(6):595-599.
Roberts, "Liposome behavior in capillary electrophoresis" Oct. 1996 Anal. Chem., 68(19):3434-40.
Sabin, "Size and stability of liposomes: A possible role of hydration and osmotic forces" 2006 Eur. Phys. J. E. 20:401-408.
SuŁkowski, "The influence of temperature, cholesterol content and pH on liposome stability" 2005 J. Mol. Struct. 744:737-747.
Swierczewska, "High-sensitivity nanosensors for biomarker detection" Apr. 2012 Chem. Soc. Rev. 41(7):2641-2655.
Tabaei, "Single lipid vesicle assay for characterizing single-enzyme kinetics of phospholipid hydrolysis in a complex biological fluid" Sep. 2013 J. Am. Chem. Soc., 135(38) :14151.
Thaxton, "Nanoparticle-based bio-barcode assay redefines 'undetectable' PSA and biochemical recurrence after radical prostatectomy" 2009 PNAS 106(44):18437-18442.
Turkevich, "A study of the nucleation and growth processes in the synthesis of colloidal gold" 1951 Discussions of the Faraday Society, 11:55-57.
Vacklin, "Phospholipase A2 Hydrolysis of Supported Phospholipid Bilayers: A Neutron Reflectivity and Ellipsometry Study" Feb. 2005 Biochemistry, 44(8):2811-2821.
Wang, "Cysteine-mediated aggregation of Au Nanoparticles: The development of a H2O2 sensor and oxidase-based biosensors" Aug. 2013 ACS Nano., 7(8):7278-86.
Willets, "Localized Surface Plasmon Resonance Spectroscopy and Sensing" May 2007 Annu. Rev. Phys. Chem. 58:267-297.
Winterhalter, "Liposome stability and formation: Experimental parameters and theories on the size distribution" 1993 Chem. Phys. Lipids 64(1-3):35-43.
Yin, "Influence of temperature, pH, and phospholipid composition upon the stability of myoglobin and phospholipid: A liposome model" Jun. 1993 J. Agric. Food Chem. 41(6):853-857.

A

B Released Cysteine

DETECTION ASSAYS AND METHODS

CROSS-REFERENCE TO RELATED APPLICATION

This application claims priority to U.S. Provisional Patent Application Ser. No. 62/121,863, filed Feb. 27, 2015, which is incorporated herein by reference.

SUMMARY

This disclosure describes, in one aspect, a method for detecting a target. Generally, the method includes providing a capture agent that specifically binds to the target, contacting a sample that includes the target with the capture agent, thereby allowing the target to bind to the capture agent, removing unbound sample, providing a recognition unit that specifically binds to the target and comprises a vesicular compartment that contains a chromogenic trigger, contacting the recognition unit with the target bound to the capture agent, thereby allowing the recognition unit to specifically bind to the target, removing unbound recognition units, contacting a lysis agent with the vesicular compartment, thereby allowing the lysis agent to lyse the vesicular compartment, releasing the chromogenic trigger, and contacting a composition that comprises a chromogenic reagent with the released chromogenic trigger, thereby allowing the chromogenic trigger to induce the chromogenic reagent to produce a colorimetric signal.

In another aspect, this disclosure describes an alternative method for detecting a target. In this aspect, the method generally includes providing a capture agent that specifically binds to the target, contacting a sample that include the target with the capture agent, thereby allowing the target to bind to the capture agent, removing unbound sample, providing a recognition unit that specifically binds to the target and comprises a primary vesicular compartment that contains an activatable lysis agent, contacting the recognition unit with the target bound to the capture agent, thereby allowing the recognition unit to specifically bind to the target, removing unbound recognition units, contacting the primary vesicular compartment with an activation agent that activates the lysis agent, thereby activating the lysis agent to lyse the primary vesicular compartment and release the lysis agent, providing a composition comprising secondary vesicular compartment, containing a chromogenic trigger, contacting the secondary vesicular compartments with the lysis agent released from the primary vesicular compartment, thereby allowing the lysis agent to lyse the secondary vesicular compartment, releasing the chromogenic trigger, and contacting a composition that comprises a chromogenic reagent with the released chromogenic trigger, thereby allowing the chromogenic trigger to induce the chromogenic reagent to produce a colorimetric signal.

In another aspect, this disclosure describes another alternative method for detecting a target. In this aspect, the method generally includes providing a capture agent that specifically binds to the target, contacting a sample that include the target with the capture agent, thereby allowing the target to bind to the capture agent, removing unbound sample, providing a recognition unit that specifically binds to the target and comprises a lysis agent, contacting the recognition unit with the target bound to the capture agent, thereby allowing the recognition unit to specifically bind to the target, removing unbound recognition units, providing a composition comprising vesicular compartments containing a chromogenic trigger, contacting the vesicular compartment composition with the lysis agent, thereby allowing the lysis agent to lyse the vesicular compartment, releasing the chromogenic trigger, and contacting a composition that comprises a chromogenic reagent with the released chromogenic trigger, thereby allowing the chromogenic trigger to induce the chromogenic reagent to produce a colorimetric signal.

In some embodiments of each method, the capture can be immobilized to a substrate.

In some embodiments of each method, the capture agent can be free in solution.

In some embodiments of each method, the capture agent can be bound to a carrier such as, for example, a metal, a particle, a liposome, or a polysome.

In another aspect, this disclosure describes an alternative method for detecting a target. Generally, the method includes providing a capture agent that specifically binds to the target, the capture agent displaceably bound to a lysis agent; contacting a sample that includes the target with the capture agent, thereby allowing the target to bind to the capture agent and displace the lysis agent; contacting a composition that includes vesicular compartments containing a chromogenic trigger with the displaced lysis agent, thereby allowing the displaced lysis agent to lyse at least a portion of the vesicular compartments, releasing the chromogenic trigger; and contacting a composition that includes a chromogenic reagent with the released chromogenic trigger, thereby allowing the chromogenic trigger to induce the chromogenic reagent to produce a colorimetric signal.

In some embodiments, the capture agent may be bound to a vesicular compartment so that (a) contacting the sample that includes the target with the capture agent and (b) contacting the composition that includes vesicular compartments containing a chromogenic trigger with the displaced lysis agent can be performed in a single step of contacting the sample with a single composition that includes the capture agent attached to a vesicular compartment.

In some embodiments, the capture agent can include a nucleic acid. In some of these embodiments, the nucleic acid can be an aptamer.

In another aspect, this disclosure describes a kit for detecting a target. Generally, the kit includes a recognition unit and a chromogenic reagent. Generally, the recognition unit includes a recognition moiety that specifically binds to the target, and a signal initiation moiety. Generally, the signal initiation moiety includes a lysis agent, a vesicular compartment that contains a chromogenic trigger, a vesicular compartment that contains an activatable lysis agent, or a vesicular compartment that includes a compound that can generate a detectable signal.

In some embodiments of the kit, the signal initiation moiety includes a lysis agent and the kit further includes a composition that includes vesicular compartments that contain a chromogenic trigger.

In other embodiments of the kit, the signal initiation moiety can include a vesicular compartment that contains a chromogenic trigger and the kit further includes a lysis agent.

In still other embodiments of the kit, the signal initiation moiety can include a vesicular compartment that contains an activatable lysis agent and the kit further includes a composition that includes an activation agent that activates the activatable lysis agent, and a composition that includes vesicular compartments that contain a chromogenic trigger.

In some embodiments of the kit, the compound that can generate a detectable signal can include an electrogenic compounds that can generate a signal detectable by an electrochemical device.

In other embodiments of the kit, the compound that can generate a detectable signal can include a fluorogenic compound that can generate a fluorescent signal. The fluorescent signal may be detectable with the naked eye or, alternatively using fluorescent microscopy.

In other embodiments of the kit, the compound that can generate a detectable signal can include a compound that can generate a chemiluminescence signal. The chemiluminescence signal may be detectable with a luminometer.

In still other embodiments of the kit, the compound that can generate a detectable signal can include an optically active compound that can generate a signal detectable by optical spectroscopy.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Bioassays with colorimetric response are convenient tools for rapid, routine, and large-scale screening of targets such as, for example, toxins and pathogens. Advantages of these assays include low cost, simplicity, and naked eye detection abilities with no requirement for skilled personnel or laboratory equipment. However, the widely used immunoassays such as ELISA suffer from low sensitivity and poor limit of detection in the order of a picomolar, which can make ELISAs ineffective for detecting low concentrations, even a single molecule or single pathogen, of target.

Alternatives techniques have been used to amplify the signal obtained from conventional bioassays including, for example, multiple enzyme attachment, stimuli-responsive and self-immolative polymers, growth of gold nanoparticles catalyzed by peroxidase, or aggregation of gold nanoparticles induced by click chemistry.

This disclosure describes a new class of colorimetric immunoassays that can allow one to detect a single target molecule or pathogen (collectively, a "single target") while keeping the assay affordable and without requiring the use of complex laboratory equipment. Visual detection of a single target is possible using a new molecular signal amplification system that converts a single ligand-receptor (or antigen-antibody) interaction into a colorimetric response that is visible to the naked eye.

The methods described herein can provide qualitative analysis of a sample—i.e., indicate with a maximum response the presence of as little as a single target in the sample. For a large number of biosensing applications in food safety, biodefense and medical diagnostics, a practical need is to know if a pathogen or toxin is present or absent in the sample, regardless of its concentration. When a single norovirus, $listeria$, HIV, anthrax, or ricin molecule is detected, an adequate treatment or prevention response can be immediately implemented with no prior need to quantification.

In order to decrease the extent of false positive reactions, one can optimize the conditions of the assay to minimize aggregation of gold nanoparticle (AuNPs) in the absence of the amplification produced by the assay. Thus, we investigated, separately, the effects of $Ca^{2+}$ concentration, pH, and protein concentration on the aggregation of AuNPs.

Effect of $[Ca^{2+}]$ on the Aggregation of AuNPs with Liposome Cysteine Solution.

Figure 3:
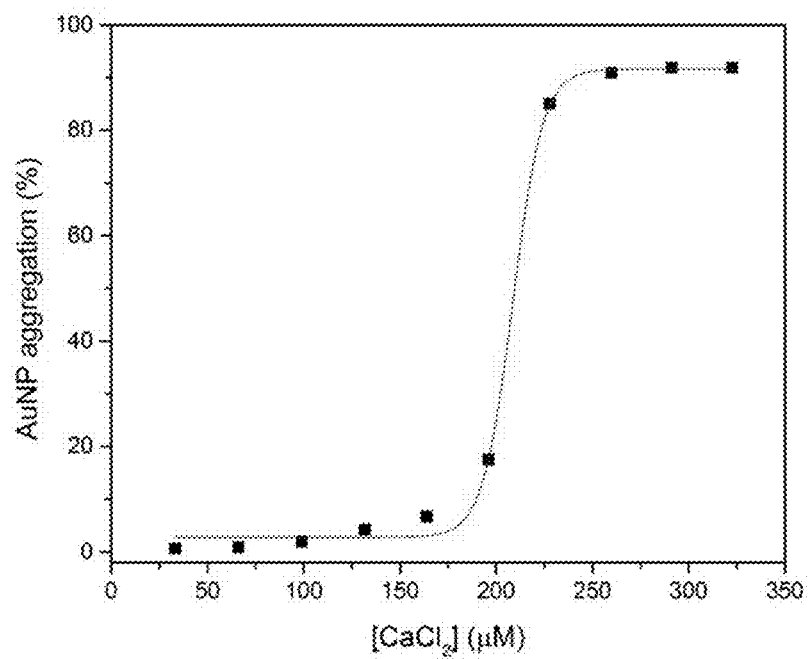
FIG. 3. Effect of $CaCl_2$ concentration on the aggregation of AuNPs in LAPIA.

The effect of $Ca^{2+}$ ($CaCl_2$) was investigated at optimum pH for $PLA_2$ activity (pH 8.5). As shown in FIG. 3, AuNPs will aggregate in a $Ca^{2+}$ concentration above 200 μM, but do not aggregate to a relevant degree in a $Ca^{2+}$ concentration below 150 μM. As a result, all the following assays were performed at $Ca^{2+}$ concentrations below 100 μM.

Effect of pH on the Aggregation of AuNPs with Liposome Cysteine Solution.

To identify the optimum pH range for the lipolysis-enhanced nanoparticle aggregation (LAPIA) assay, we investigated the effect of pH on the stability of the assay in the absence of the enzyme $PLA_2$. A mixture containing cysteine-loaded liposomes, $Ca^{2+}$ (66 μM), and AuNPs was prepared at different pHs. FIG. 4A shows the aggregation of AuNPs is observed at pH below 6.45 and, but stable at pH greater than 6.7. A control containing the same mixture but without cysteine did not show any aggregation, indicating that low pH caused lysis of the liposomes and release of cysteine which causes the aggregation. As a result, the pH of the mixture in performing a LAPIA test can be in the range of 6.45-9.0 such as, for example, pH 7.0-8.5, which includes the optimum pH for $PLA_2$ activity (pH 8.5). Thus, in some embodiments, a lipolysis-enhanced nanoparticle aggregation may be performed using synthesized AuNPs adjusted to pH 8.5.

Effect of IgG, BSA and $PLA_2$ on the Stability of Liposomes and Aggregation of AuNPs Since protein molecules also can cause aggregation of AuNPs, we investigated the effect of different concentration of IgG, BSA, and $PLA_2$ on the aggregation of AuNP. The experiment was performed at pH 8.5 in a LAPIA mixture containing AuNPs, cysteine-encapsulated liposomes (20 mM) and the protein of interest, with no $Ca^{2-}$ added. FIG. 4F shows that BSA has negligible effect on AuNPs even at high concentrations. IgG cause a very low aggregation (<1%) at the concentrations used in the LAPIA test (FIG. 4F). $PLA_2$ can cause complete aggregation at concentrations greater than 1.0 U/mL even without $Ca^{2+}$, but has a negligible effect (<1% aggregation) at a concentration of up to 0.5 U/mL. $PLA_2$ therefore requires the presence of $Ca^{2+}$ to be meaningfully active (e.g., aggregate AuNPs) when present at concentration below 1 unit/mL.

Figure 7:
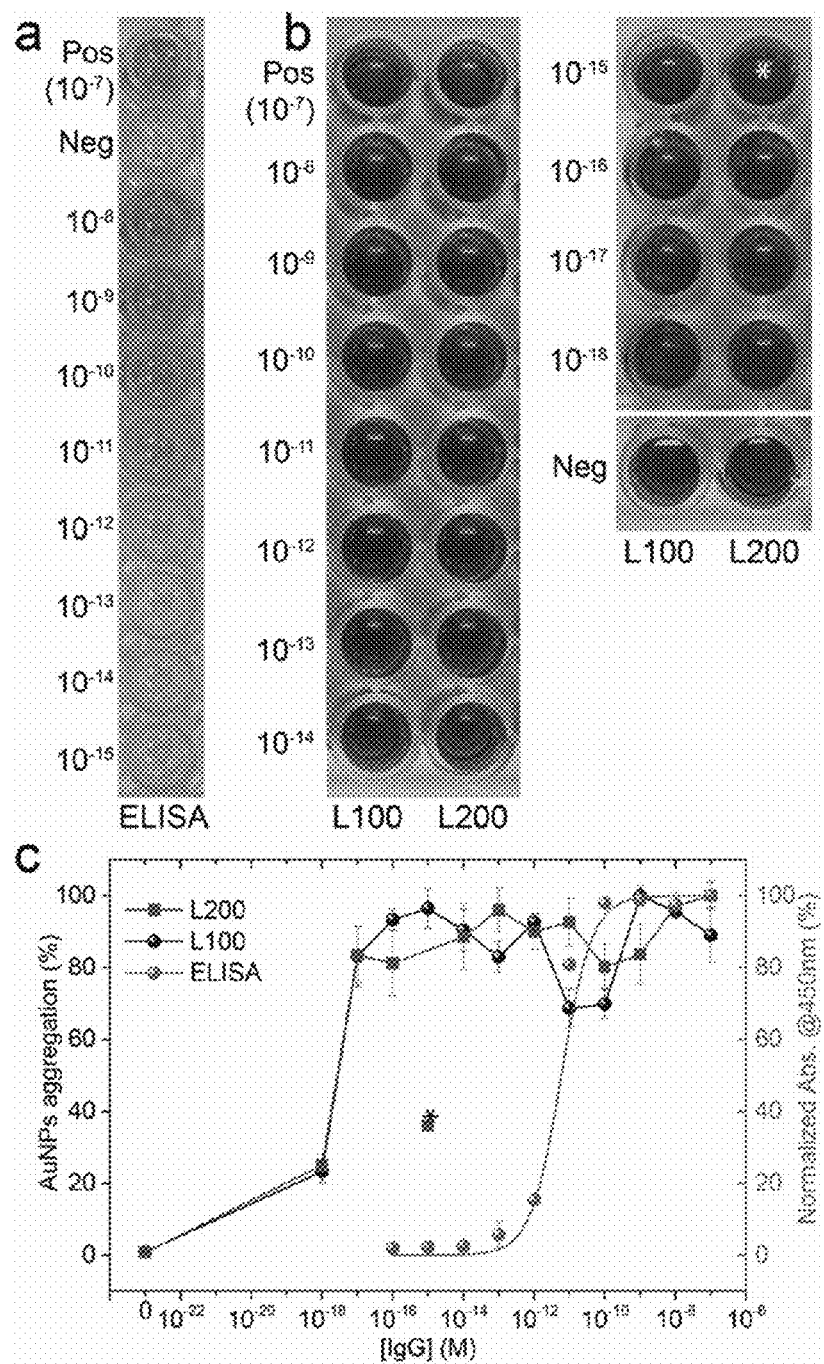
FIG. 7. Naked-eye detection of rabbit IgG proteins at different concentrations. (A) Conventional ELISA. Color change is caused by the biocatalysis of 3',5,5'-tetramethylbenzidine (TMB) by horseradish peroxidase. The detection limit is at the picomolar level ($10^{-12}$ M). (B) LAPIA test. The assay was performed using 100 nm (L100) and 200 nm (L200) liposomes. All tests showed maximum color shift from red to dark blue at extremely low concentrations down to $6.7 \times 10^{-17}$ M. A concentration of $6.7 \times 10^{-18}$ M causes 25% aggregation and can still be distinguished from the control. (C) Comparison of the colorimetric response of conventional ELISA and LAPIA tests at different target IgG concentrations. The percentile of AuNPs aggregation in LAPIA test is represented with respect to negative control by measuring the optical density at 655 nm. The colorimetric signal of ELISA was recorded at 450 nm. The microwell and corresponding data point indicated with a star represent a false negative. Neg: negative control, Pos: positive control. The concentrations are indicated in molarity (M).

FIG. 7 shows the results of an IgG detection experiment that compares a conventional ELISA assay with a LAPIA immunoassay (FIG. 1) using two liposomes of two different sizes. The detection limit of conventional ELISA is in the picomolar level ($10^{-12}$ M), while LAPIA immunoassays exhibit detection limits at the attomolar level ($10^{-18}$ M). Since the response is binary (i.e., all-or-none), the only obstacle for the detection limit is the volume of the sample. A lower limit of detection (zeptomolar, $10^{-21}$ M) can be obtained with adequate sample delivery or dilution.

Thus, this disclosure describes an immunoassay platform that can provide sensitive binary detection of a target such as, for example a molecule (e.g., a toxin, a contaminant, or other molecule of interest) or a pathogen (e.g., a bacterium, virus, parasite, etc.). Unlike a conventional ELISA immunoassay, where the color is generated by enzyme catalysis of a chromogenic substrate, the methods described herein use plasmonic colorimetry to generate a detectable signal that can be detected by the naked eye. The color change can be caused by nanoparticle aggregation. Also in contrast to a conventional ELISA immunoassay, embodiments that use an enzyme for signal amplification do not require that the enzyme is immobilized to an antibody. In the methods described herein, the assay may be performed without using an enzyme or, in some embodiments, the enzyme can be encapsulated in liposomes rather than bound to an antibody. The free enzyme provides better performance than an immobilized enzyme (e.g., in a conventional ELISA or plasmonic ELISA).

These features of the methods described herein provide the ability to rapidly detect a target in a sample using a low cost, assay that does not require specialized equipment or a high degree of specialized technical skill. Thus, the methods may be employed in a wide variety of applications by a wide variety of users. Exemplary applications include, for example, food safety, detection of food spoilage or adulteration, environmental testing, medical diagnosis, biodefense, and biological and medical imaging (e.g., immunohistology).

The methods described herein can be used to confirm the absence of, for example, any pathogen (e.g., bacterium, virus, parasite, etc.) or molecule (e.g., toxin, contaminant, etc.) in food during processing or storage. The amplification system employed by the methods represents an extremely sensitive assay that can specifically detect the presence of a pathogen or molecule independent of its concentration. This can be useful where there may be a "zero tolerance" threshold for a particular pathogen or molecule.

The methods also can be applied to environmental monitoring of trace chemicals. Thus, the assays may be performed, for example, after wastewater treatment or other liquid sample in order to detect the presence of pollutants, toxins, or other contaminants. A related application can involve detecting bioterrorism agents that may be present in a particular environment at low concentrations.

The methods described herein also can be used as a medical diagnostic test. The assay could be used for detecting infectious agents such as HIV in serum, urine, or oral fluids, only a few days after the infection, as opposed to three months post-infection as is required with the current ELISA tests. For early diagnostic applications, while the commercially available HIV point-of-care or self-testing assays are targeting the rapidity or time needed to perform the test, the methods described herein, because of the increased sensitivity possible, can reduce the time between first infection and when the test can reliably detect that infection. This aspect of the methods described herein responds to an important need of the public, healthcare agencies, and patient care organizations.

Figure 5:
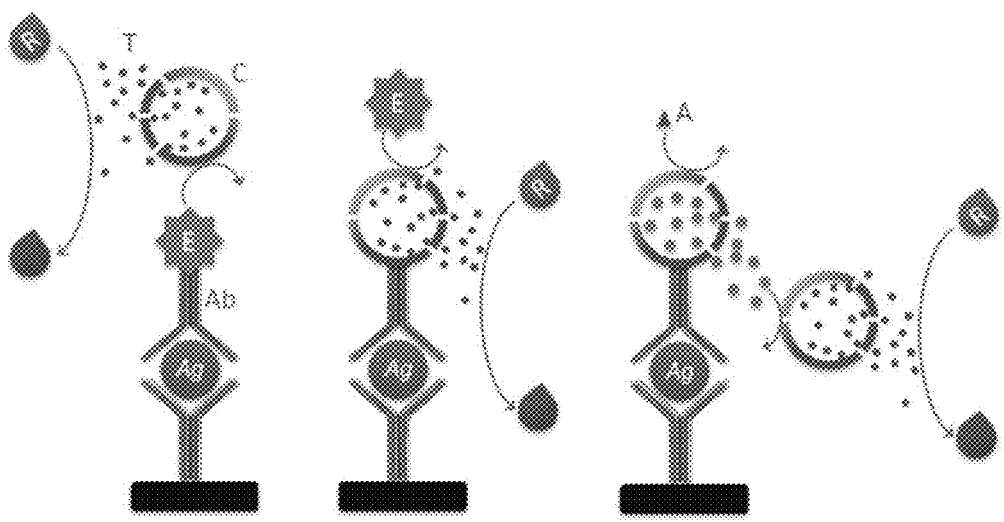
FIG. 5. Schematic diagram of various embodiments of Liposome-Enhanced ImmunoAssay.

One exemplary embodiment of a lipolysis-enhanced nanoparticle aggregation immunoassay is shown as Assay 1 in FIG. 5. In the illustrated embodiment, a capture agent is immobilized to a substrate. The capture agent is selected to specifically bind to the target. As used herein, the term "specific" and variations thereof (e.g., "specifically" bind) refer to having a differential or a non-general affinity, to any degree, for a particular target. The capture agent may be, for example, an antibody, aptamer, protein, receptor, biomolecule, a nucleic acid (e.g., RNA or DNA), or any other agent that specifically binds to the target to be detected.

The target can be any target of interest including a pathogen such as, for example, a bacterium, virus, fungi (e.g., molds or yeasts), or parasite. The target also can include an infectious agent (e.g., a prion), a molecule that can represent a toxin, a contaminant, a pollutant, a biomarker, a molecule that is a component of a eukaryotic cell or tissue (e.g., as in biopsy analysis or histological imaging applications), a nucleic acid (e.g., RNA or DNA), or other molecule of interest.

A sample to be analyzed can be contacted with the capture agent under conditions effective to allow the target, if present in the sample, to bind to the capture agent. Unbound sample is washed from the assay.

A composition that includes a recognition unit is contacted with the assay under conditions effective to allow the recognition unit to bind to the target captured by the capture agent. In some cases, the capture agent and the recognition unit may be related or the same, except that the recognition unit is functionally attached (e.g., conjugated) to a lysis agent. Thus, the recognition unit can include, for example, any antibody, aptamer, protein, single stranded DNA, receptor, or any other agent that specifically binds to the target to be detected. Unbound recognition unit is washed from the assay.

The lysis agent can be any molecule that has the ability to specifically break down a vesicular compartment (e.g., a liposome), thereby prompting release of the contents of the vesicular compartment. Depending upon the particular embodiment of the assay, the lysis agent can be an enzyme such as, for example, a hydrolase or a lyase. Thus, exemplary enzymes include, for example, a phospholipase or lysozyme. The lysis agent can also be a detergent or surfactant such as, for example, polysorbate (e.g., TWEEN, ICI Americas, Inc., Wilmington, Del.), TRITON X (Dow Chemical Co., Midland, Mich.), sodium dodecyl sulfate (SDS), NP-40, BRIJ (Uniqema Americas LLC, Wilmington, Del.), polyoxyethylene-based detergents, glycoside-based detergents (e.g., octyl glucoside or octyl thioglucoside), zwitterionic detergents (e.g., 3-[(3-cholamidopropyl)dimethylammonio]-1-propanesulfonate (CHAPS) or 3-([3-Cholamidopropyl]dimethylammonio)-2-hydroxy-1-propanesulfonate (CHAPSO)). The lysis agent can also be physical or mechanical (e.g., temperature or pressure), or due to changes in the chemical environment in the assay (e.g., a change in pH or ionic strength).

A composition that includes vesicular compartments (e.g., liposomes, as illustrated in FIG. 5) that contain a chromogenic trigger is contacted with the assay under conditions effective for the lysis agent such as phospholipase enzymes attached to the recognition unit to lyse the, causing the liposomes to release the chromogenic trigger. The liposome composition can also include a chromogenic reagent that produces a colorimetric signal in the presence of the chromogenic trigger. Alternatively, the chromogenic reagent can be provided in a separate composition and added to the assay before, at the same time as, or after the liposome composition is added. In either case, the chromogenic trigger can induce the chromogenic reagent to generate a color signal that can be visible to the naked eye.

In some embodiments, the chromogenic trigger can include, for example, cysteine, which can induce the aggregation of gold nanoparticles (AuNPs). In alternative embodiments, however, the chromogenic trigger can include, for example, any organic, inorganic, or hybrid agent that triggers a chromogenic reaction in specific conditions. Suitable agents include, for example, molecular crosslinkers (e.g., amino-thiolated molecules other than cysteine), pH indicators, acid/basic molecules, organic ions, and metal ions.

In some embodiments, the chromogenic reagent can include nanoparticles (e.g., gold nanoparticles) that aggregate in the presence of the chromogenic trigger (e.g., cysteine). In alternative embodiments, however, the chromogenic reagent can include any organic, metal, or hybrid molecule or particle that has the ability to generate color in certain conditions through a chromogenic reaction. Exemplary chromogenic reactions include, for example, nanoparticle aggregation (plasmonic colorimetry), chromogenic transition of polydiacetylenes, transition of pH indicators, or chromogenic supramolecular assembly.

Figure 1:
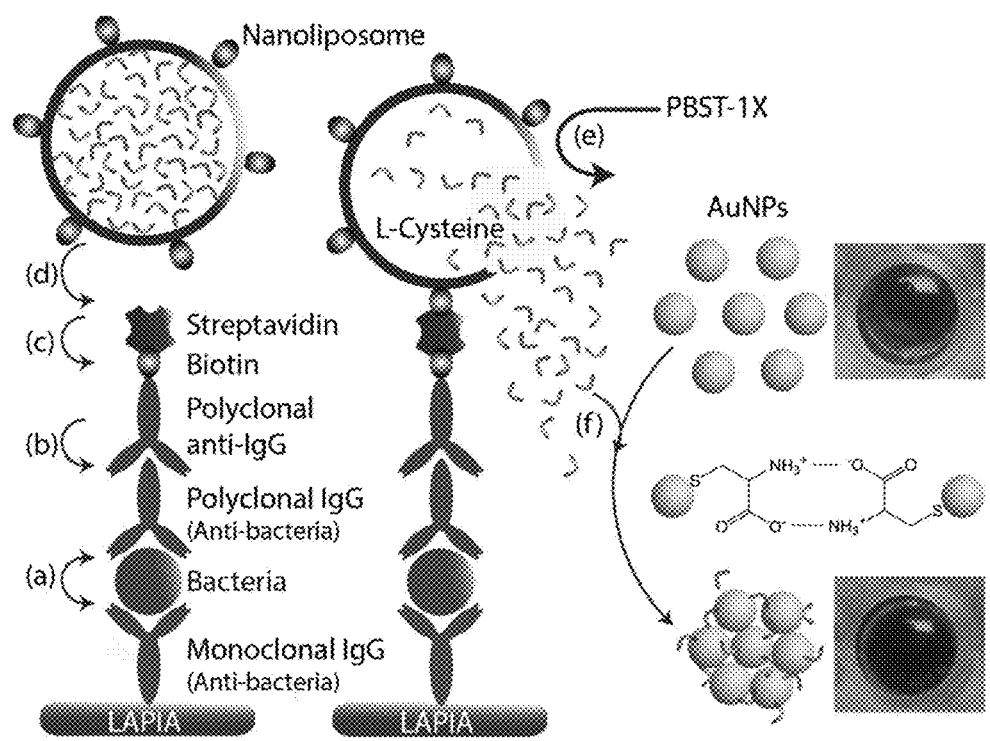
FIG. 1. An exemplary embodiment of a Liposome-Amplified Plasmonic ImmunoAssay (LAPIA). A single microbe (e.g., a virus, a bacterium, a fungus, or a parasite), infectious agent (e.g., prion), or molecule (e.g., toxin or antigen) can rapidly trigger a chromogenic chemical cascade chain reaction. (1) Capture of the target (e.g., antigen, pathogen, molecule) using direct or sandwich immunoassay. (2) After washing steps, Biotin-conjugated IgG is added to the LAPIA plate to interact with the immunocomplex. (3) After incubation and washing, streptavidin is added to interact with biotin and bind to IgG. (4) Biotin-conjugated liposomes containing cysteine is added to the medium followed by addition of a gold nanoparticle (AuNPs) solution. (5) Addition to PBS-TWEEN 1× to the plate, which causes the breakdown of liposomes and release of cysteine, leading to the aggregation of gold nanoparticles and color shift from red to blue-violet or grey (6).

A second exemplary embodiment of a lipolysis-enhanced nanoparticle aggregation assay is illustrated in FIG. 1 and in FIG. 5 (Assay 2). In this embodiment, the lysis agent is not attached to the recognition unit, but is instead provided free in a composition that is added to the assay. The recognition unit is instead attached to a liposome that contains the chromogenic trigger. This attachment can be direct (e.g., using a crosslinker between the liposome and the recognition unit) or indirect (e.g., by functionalizing the liposome and recognition unit with biotin and add streptavidin to assemble them).

The sample is contacted with the capture agent, washed, contacted with the recognition unit, and washed as described above. FIG. 5 (Assay 2) shows the assay in a generalized schematic, while FIG. 1 shows a particular embodiment in more detail. FIG. 1 shows the use of a recognition unit that includes an IgG that specifically binds to the target and a biotin-conjugated secondary anti-IgG antibody that binds to the IgG bound to the target. The liposome is conjugated to streptavidin, which specifically binds to the biotin, thus attaching the liposome to the recognition unit.

In this embodiment, a composition that includes a lysis agent is added to the assay under conditions effective to allow the lysis agent to lyse the liposomes bound to the target (through the recognition unit). In the particular embodiment illustrated in FIG. 1, a composition that includes a detergent (TWEEN, ICI Americas, Inc., Wilmington, Del.) is used as the lysis agent. The lysis agent disrupts the liposome, causing release of the chromogenic trigger that had been contained in the liposome. In the embodiment illustrated in FIG. 1, the chromogenic trigger is cysteine, which induces aggregation of gold nanoparticles (AuNPs), which, in turn, causes a color change from red to blue.

Figure 2:
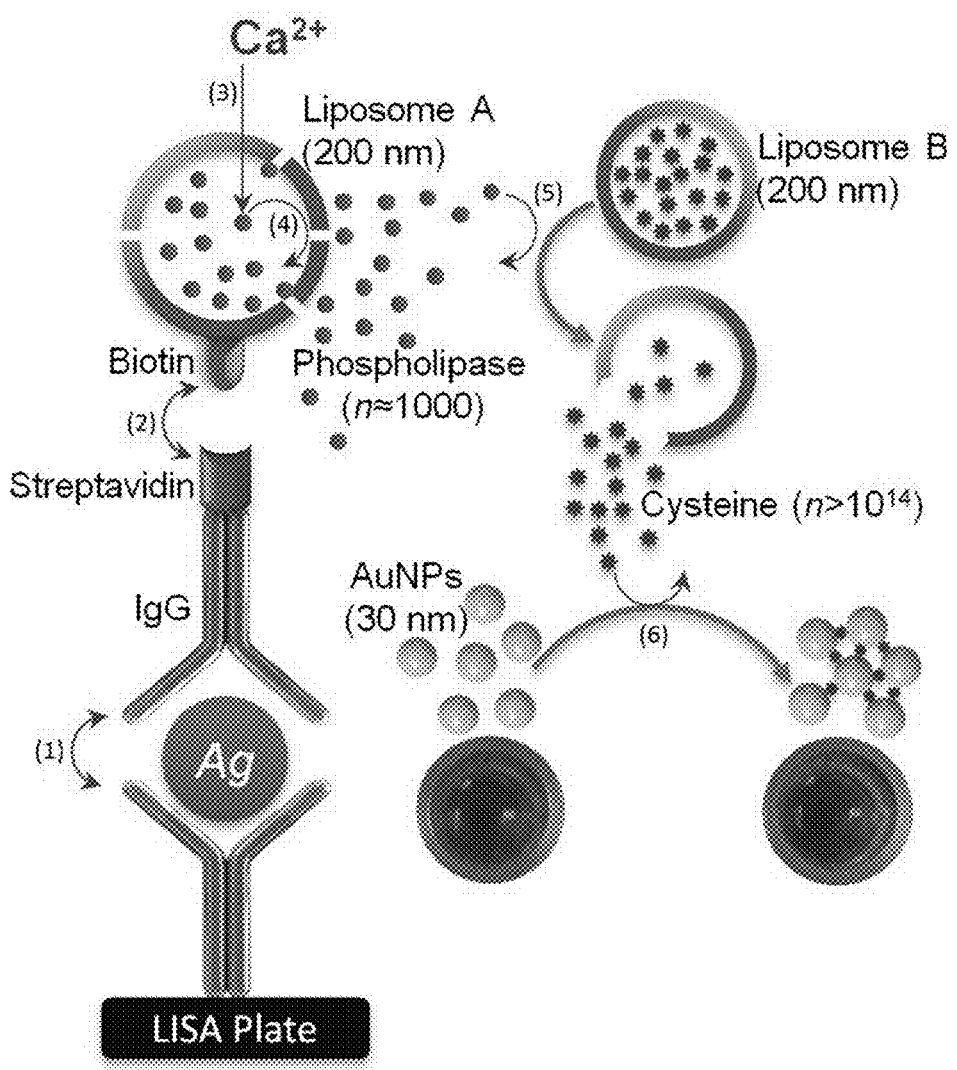
FIG. 2. An exemplary embodiment of a Liposome Chain Reaction (LCR)-based Immunoassay. This class of assay includes two levels of amplification using primary and secondary liposomes. (1) Capture of the target (antigen, pathogen, molecule) using direct or sandwich immunoassay. (2) Primary liposome containing $PLA_2$ enzymes is allowed to interact with the immunocomplex through biotin-streptavidin interaction. (3) After washing steps, calcium ($Ca^{2+}$) is added to the assay. (4) $Ca^{2+}$ diffuses inside the primary liposome (Liposome A) to activate the $PLA_2$, which breaks down the liposome and is then released into the medium. (5) The released $PLA_2$ breaks down the secondary liposome (Liposome B), thus causing the release of the loaded cysteine molecules. (6) The released cysteine causes aggregation of the gold nanoparticles and change in color from red to blue.

A third exemplary embodiment of a lipolysis-enhanced nanoparticle aggregation is illustrated in FIG. 2 and in FIG. 5 (Assay 3). This embodiment uses primary and secondary liposome to generate a chemical cascade that can amplify the signal and, therefore, increase the sensitivity of the assay.

The sample is contacted with the capture agent, washed, contacted with the recognition unit, and washed as described above. FIG. 5 (Assay 3) shows the assay in a generalized schematic, while FIG. 1 shows a particular embodiment in more detail. FIG. 1 shows a recognition unit that includes a streptavidin-conjugated IgG that binds to the target that has been captured by the capture agent. A biotin-conjugated primary liposome is contacted with the assay under conditions effective to allow biotin-streptavidin affinity to attach the biotin-conjugated primary liposome to the streptavidin-conjugated IgG. Unbound biotin-conjugated primary liposome is washed from the assay.

The primary liposome contains the lysis agent—in this case, an activatable lysis agent such as the enzyme phospholipase ($PLA_2$). A composition that includes an activation agent is contacted with the assay under conditions effective for the activation agent to activate the lysis agent. In the embodiment illustrated in FIG. 2, the activation agent includes $Ca^{2+}$ ions, which can diffuse into the primary liposome and activate the phospholipase. In other embodiments, however, the activation agent can be any molecule (e.g., a cofactor or co-enzyme) that can activate the lysis agent (e.g., an enzyme).

The assay also involves a composition that includes secondary liposomes that contain the chromogenic trigger (e.g., cysteine, as shown in FIG. 2) and a composition that includes the chromogenic reagent (e.g., gold nanoparticles, AuNPs, as shown in FIG. 2). As with the alternative embodiments discussed above, the compositions can be provides sequentially in any suitable order. Alternatively, two or more of the $Ca^{2+}$-containing composition, secondary liposome composition, and/or chromogenic reagent composition can be provided together.

In the particular embodiment shown in FIG. 2, $Ca^{2+}$ ions diffuse across the membrane of the primary liposome and activate the phospholipase. The phospholipase disrupts the primary liposome and thereby escapes from the primary liposome. The released phospholipase is therefore free to disrupt the secondary liposome that contains the cysteine chromogenic trigger, thereby releasing the cysteine. The free cysteine can then induce aggregation of the gold particles, causing a color change from red to blue.

In the embodiment illustrated in FIG. 2, the amplification possible is significant. Each primary liposome of, for example, 100 nm diameter can release approximately 1000 phospholipase molecules, each of which can lyse multiple secondary liposomes. Each secondary liposome can release billions of cysteine molecules, which induce aggregation of gold nanoparticles and the color change that can be visible to the naked eye. Thus, it is possible that an assay can accurately detect a single target bound to a capture agent. This detection can be further enhanced by using larger liposomes (200 nm or 400 nm) to contain more enzymes and more cysteine molecules.

Figure 9:
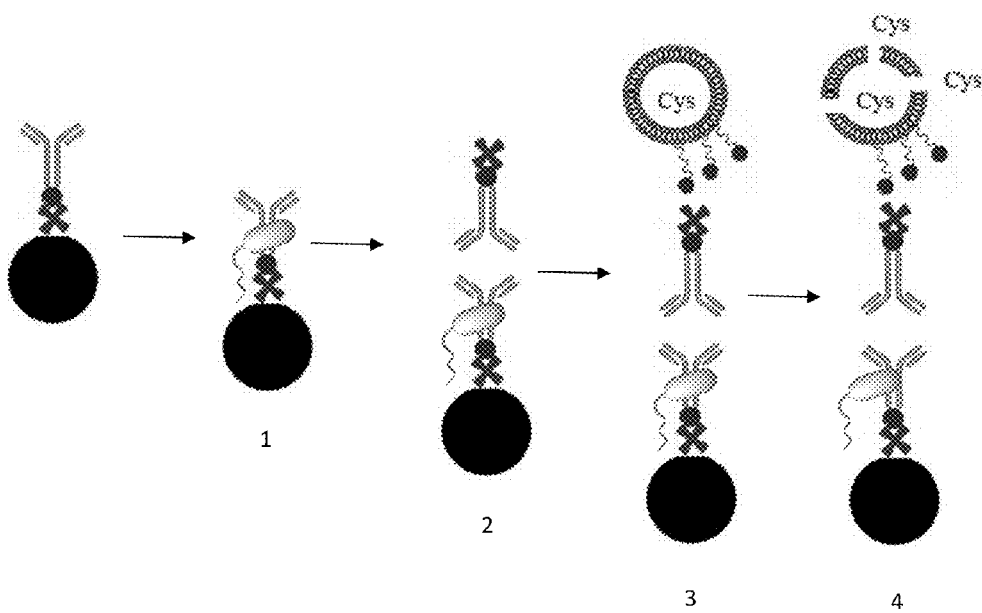
FIG. 9. (A) Steps of the detection process using magnetic beads and aptamers. 1. Pathogen capture by the antibody conjugated magnetic particle. 2. Addition of anti-$E.$ $coli$ antibodies and streptavidin to construct the pathogen linked "bridge." 3. Addition of biotinylated liposomes that contain cysteine. 4. Lysis of the liposomes and release of cysteine. (B) Color change gold nanoparticles undergo in the presence of cysteine.
Figure 9:
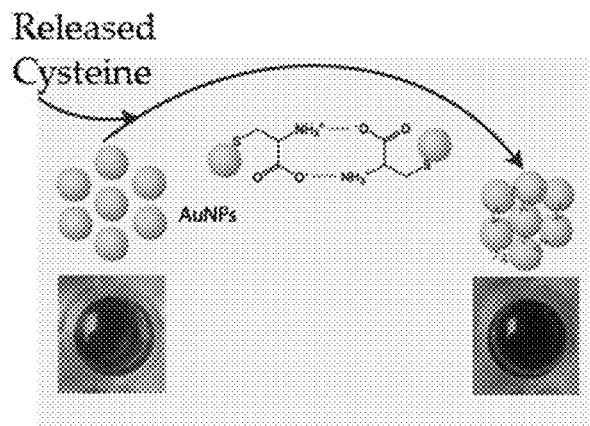

Another alternative embodiment is illustrated in FIG. 9. This embodiment may be particularly suited for detecting foodborne pathogens. The embodiment illustrated in FIG. 9 uses liposome-encapsulated cysteine to amplify a colorimetric signal. (Bui et al., 2015, *Nano letters* 15(9): 6239-6246) and magnetic $Fe_3O_4$ nanoparticles. Briefly, as illustrated in FIG. 9, anti-pathogen antibodies can be attached to magnetic particles using a biotin-streptavidin linkage.

Figure 11:
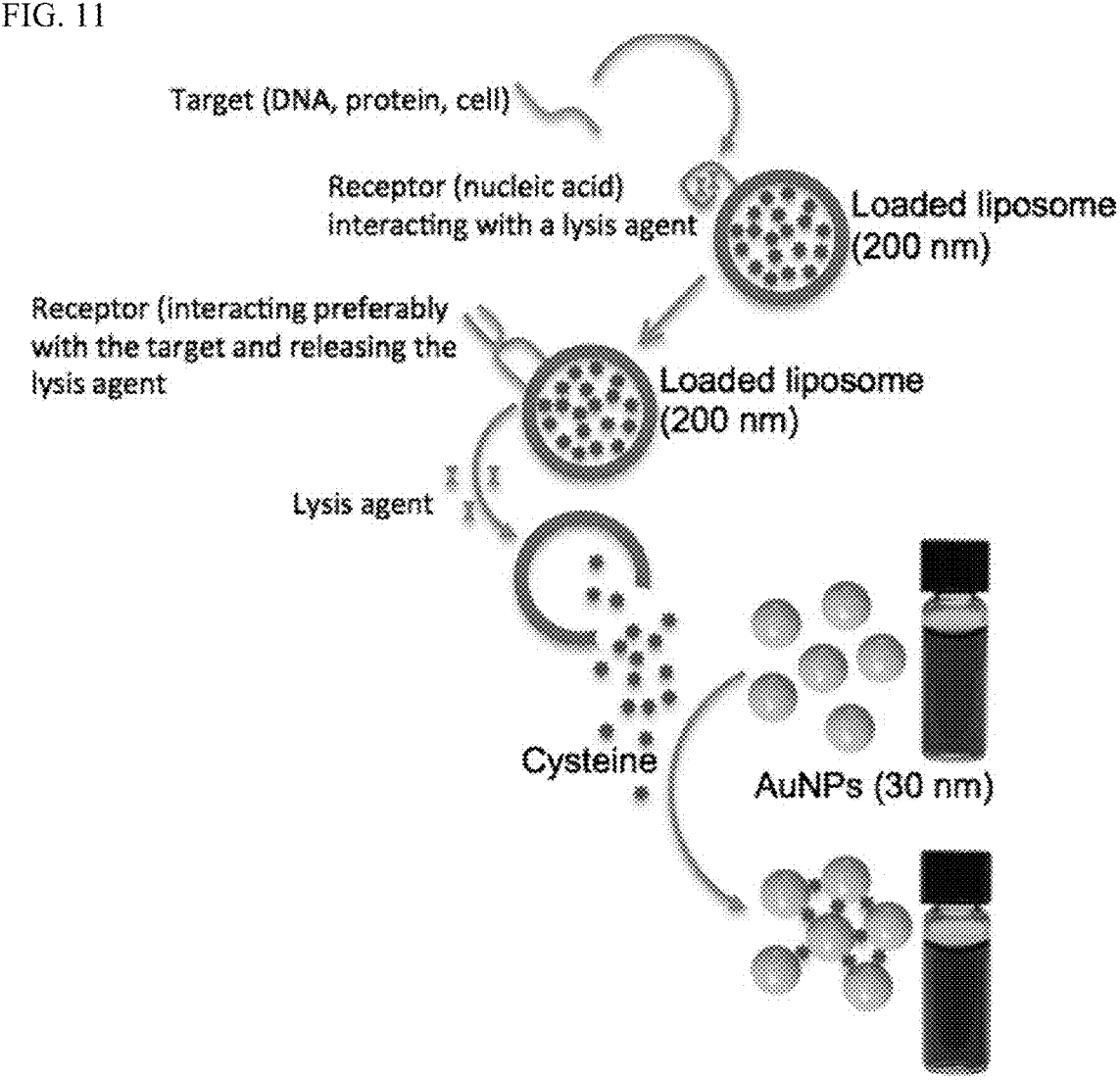
FIG. 11. Homogeneous version of liposome-amplified plasmonic assay. The liposomes are functionalized with nucleic acid receptors interacting weakly with a lysis agent. The presence of the target in the sample leads to interaction between the receptor and the target, which disrupts the interaction between the receptor and the lysis agent, resulting in release of the lysis agent and the breakdown of the liposomes. The release of cysteine by the liposomes will cause the aggregation of gold nanoparticles and color shift of the solution from red to dark blue. This test does not require the immobilization of the target.

A fourth exemplary embodiment, illustrated in FIG. 11, generally includes the use of a capture agent that specifically binds to the target and is displaceably bound to a lysis agent. A sample is contacted with the capture agent, thereby allowing any target in the sample to bind to the capture agent and displace the lysis agent. A composition that includes vesicular compartments containing a chromogenic trigger is then contacted with the displaced lysis agent, thereby allowing the displaced lysis agent to lyse at least a portion of the vesicular compartments, releasing the chromogenic trigger. The released chromogenic trigger can then contact a composition that includes a chromogenic reagent, thereby allowing the chromogenic trigger to induce the chromogenic reagent to produce a detectable signal.

For initial testing, a non-pathogenic strain of *E. coli* was used (ATCC:25922) as a model microbe. Magnetic particles containing anti-*E. coli* antibodies were mixed with sample solutions, allowing the antibodies to bind microbes in the sample as shown in FIG. 9A-1. After this incubation, the magnetic particles were separated from the solution, washed, and blocked. Biotinylated anti-*E. coli* antibodies were then added to the particles. In the presence of the targeted microbe, a biomolecular "bridge" including captured pathogen is created, as shown in FIG. 9A-2.

Figure 4:
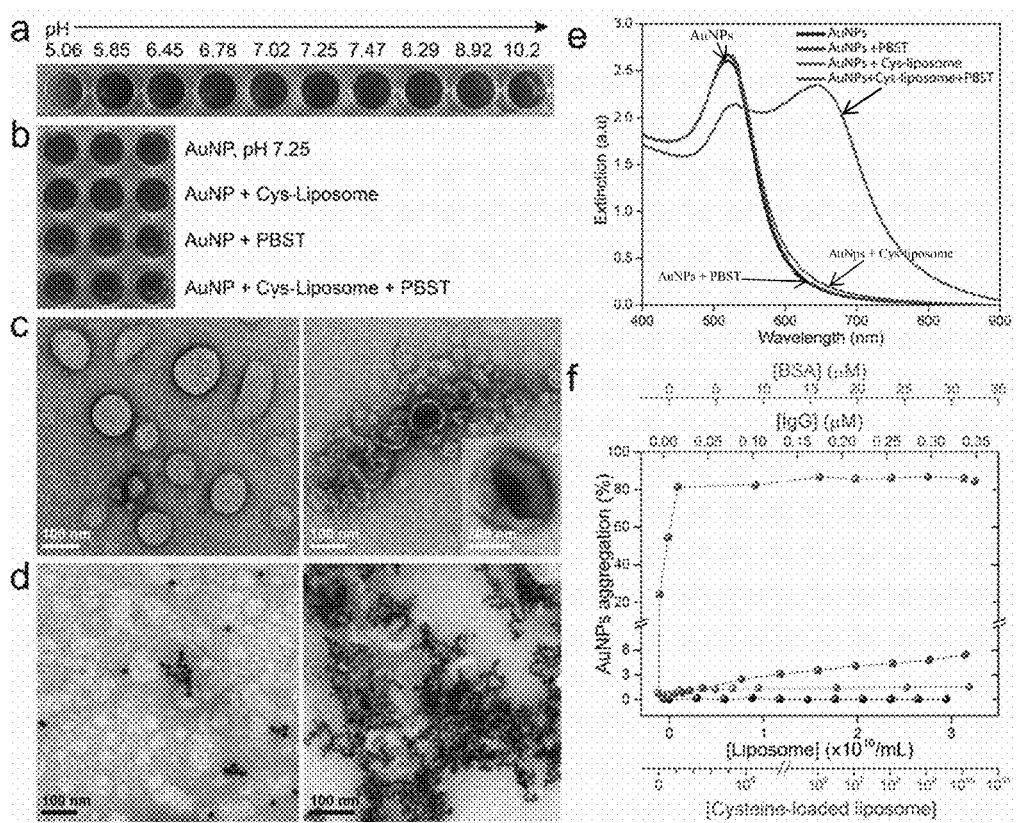
FIG. 4. Characterization of the LAPIA test. (A) Optical photograph of AuNPs aggregation at different pH values in the presence of cysteine-loaded liposomes (Cys-liposomes) without PBST. The mixture is stable at pH greater than 6.7. (B) Photograph showing the aggregation of AuNPs upon introduction of PBST 1×. The PBST breaks liposomes and releases cysteine, resulting in total aggregation of AuNPs and visible color change from red to dark blue. The addition of PBST without Cys-liposomes does not cause aggregation. (C) TEM images of intact liposomes (left) and lysed liposomes after exposition to PBST (right). The Inset shows a higher magnification image of Cys-liposome after hydrolysis by PBST. (D) TEM images of AuNPs (pH 7.25) with Cys-liposome solution, before (left) and after (right) adding PBST. (E) UV-vis absorption spectra of single AuNPs in the absence and presence of Cys-liposome and PBST solution. Single AuNPs are characterized by a single absorption peak at around 520 nm. The addition of PBST caused the appearance of a second band between 600 and 700 nm with a maximum at around 650 nm, characteristic of aggregated or assembled nanoparticles. (F) Effect of BSA, IgG, and non-loaded liposomes on the stability of AuNPs. At concentrations used in typical bioassays, the aggregation is less than 2%. The addition of Cys-liposome and PBST cause total AuNPs aggregation (>80%), regardless of the concentration of the liposomes. The number of Cys-liposomes plotted in the graphic is the number needed to cause the aggregation of 100 µL AuNPs solution.

Biotinylated cysteine-encapsulating liposomes were added to the particle solution (FIG. 9A-3). Gold nanoparticles and phosphate buffer containing Tween-20 were added. The Tween-20 breaks the liposomes attached to the nanoparticle through the microbe "bridge" and releases the cysteine payload (FIG. 9A-4). The free cysteine then induces the aggregation of gold nanoparticles, which yields a distinct red-to-blue color change (FIG. 9B). If the target microbe is not present in the system, then the antibodies and liposomes are simply washed away and the gold remains red upon addition of Tween-20.

Figure 10:
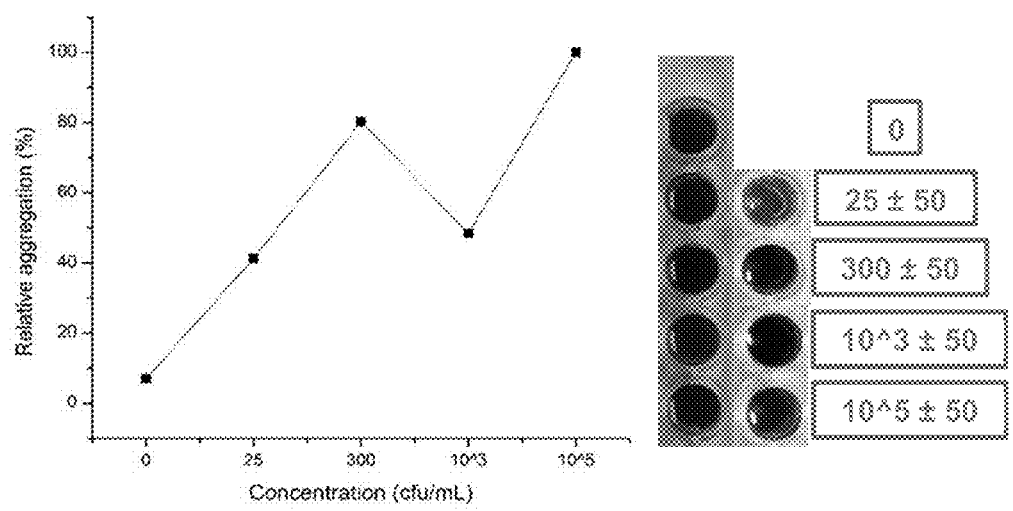
FIG. 10. Graph showing the relationship between number of bacterial colony forming units (cfu) and color change in the gold nanoparticles.

FIG. 10 shows results of tests using different concentrations of target microbe estimated via optical density at 600 nm. Color changes were assessed as a percentage of gold nanoparticle aggregation analyzed via UV-visible spectroscopy. Greater liposome capture, as facilitated by the presence of the target pathogen, results in a greater color change from red to blue.

In some embodiments, however, one can use a sensing scheme based on DNA aptamers. An aptamers is a small strand of DNA or RNA that can bind to a specific molecule. Aptamers can offer certain advantages over antibodies as a detection assay reagent. First, aptamers can be more cost effective to produce than antibodies. Second, aptamers can bind to target molecules with superior selectivity.

Thus, for example, a DNA aptamer may be deposited onto the surface of magnetic nanoparticles. In some embodiments, the aptamer may be designed to detect a foodborne pathogen. An aptamer that specifically binds a particular target may be synthesized, labelled with biotin, and used in place of the antibody in the scheme illustrated in FIG. 9. An aptamer may be attached to a nanoparticle using the same conditions discussed above in the context of attaching an antibody to the nanoparticle.

While described above in the context of particular exemplary embodiments, other embodiments are possible. For example, cysteine can be replaced as the chromogenic trigger with an alternative generator of a detectable signal such as, for example, an enzyme (e.g., such as peroxidase (HRP) that can generate colorimetric response by substrate catalysis), a redox mediator (which can generate amplified electrical current for an electrochemical sensor), or a fluorogenic molecule that can generate fluorescence. Thus, while the lipolysis-enhanced nanoparticle aggregation assays described above are described in terms of plasmonic colorimetry tests for qualitative analysis, these assays can be readily modified to involve either enzymatic, fluorescent, chemiluminescent, or electrochemical detectable signals that can allow the assays to be adapted for quantification.

As another example, while the various embodiments are illustrated in the context of the capture agent being immobilized to substrate, the methods may be performed using a capture agent that is free in solution or is attached to a carrier dissolved or suspended in a reagent medium. The capture agent may be attached to, for example, a metal, an organic particle, and inorganic particle, a nanoparticle, a liposome, or a polysome. For example, FIG. 11 illustrates an exemplary embodiment in which a nucleic acid receptor attached to a liposome acts as a capture agent for a target (e.g., DNA, protein, or cell).

In the embodiment shown in FIG. 11, the nucleic acid capture agent is bound to a carrier that, in this case, is a liposome that contains the chromogenic trigger. In this embodiment, therefore, it is possible to combine certain steps to streamline the method. For example, with the capture agent bound to a carrier that contains the chromogenic trigger, contacting the sample with the capture agent also contacts the sample with the vesicular components containing the chromogenic trigger. In this and other exemplary embodiments expressly described herein, it can be possible to combine two or more steps by providing a single composition that includes two or more assay reagents.

As another example, while the various embodiments are illustrated in the context of the vesicular compartment being a liposome, the methods may be performed using a vesicular compartment that includes, for example, a polymersome, a dendrosome, or any other supramolecular compartment that is lysable using a suitable lysis agent.

In another aspect, this disclosure describes kits that provide components required to perform an embodiment of the assay described above. Thus, the kit can include a recognition unit and a chromogenic reagent. Generally, the recognition unit includes a recognition moiety that specifically binds the target. The recognition unit also includes a signal initiation moiety that can vary with the particular embodiment of the assay method one chooses to perform.

In one embodiment, therefore, the kit can include a signal initiation moiety that includes a lysis agent. In such embodiments, the kit can then further include a composition that includes liposomes that contain a chromogenic trigger and that can be lysed by the lysis agent to release the chromogenic trigger.

In an alternative embodiment, the kit can include a signal initiation moiety that includes a liposome that contains a chromogenic trigger. In such embodiments, the kit can further include a lysis agent that can lyse the liposomes in the signal initiation moiety to release the chromogenic trigger.

In yet another alternative embodiment, the kit can include a signal initiation moiety that includes a liposome that includes an activatable lysis agent. In such embodiments, the kit can further include a composition that includes an activation agent that activates the activatable lysis agent. The kit also can include a composition that includes liposomes that contain a chromogenic trigger. The activation agent can enter the liposome of the signal initiation moiety to activate the activatable lysis agent, which then lyses the signal initiation moiety liposome and is released into the assay solution. The activated lysis agent can then lyse the liposomes that contain the chromogenic trigger.

In various embodiments, at least one kit component—e.g., the vesicular compartment—can be lyophilized or freeze dried. Thus, the lyophilized or freeze dried kit component may be provided in the kit in powder form, then dissolved in a buffer solution prior to use.

As used herein, the term "and/or" means one or all of the listed elements or a combination of any two or more of the listed elements; the terms "comprises" and variations thereof do not have a limiting meaning where these terms appear in the description and claims; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

The following examples demonstrate the use of lipolysis-enhanced nanoparticle aggregation immunoassays with plasmonic colorimetry.

Example 1—Synthesis of Cysteine-Encapsulated Liposomes

L-cysteine-encapsulated liposomes were prepared using a reverse-phase evaporation method. (Gomes et al., 2006, Langmuir 22:7755-7759; An et al., 2009, J Collid Interface Sci., 331:98-103) Briefly, 5 mg of L-α-phosphotidylcholine (Egg PC, Avanti Polar Lipids, Inc., Alabaster, Ala.) was dissolved in 1 mL chloroform (Sigma-Aldrich, St. Louis, Mo.) solution. Solvent was evaporated to form thin layer of PC under nitrogen flow and vacuum for 15 minutes to ensure that solvent is evaporated completely. Thin film of PC was rehydrated with 5 mL of L-cysteine (20 mM, Sigma-Aldrich, St. Louis, Mo.) solution in NANOPURE water (Thermo Fisher Scientific, Waltham, Mass.) to obtain 1 mg/mL final concentration of liposome. Multiplayer liposomal vesicles were vortexed until the solution become cloudy, then sonicated for one minute at room temperature. Multilayer liposomal vesicles with difference sizes were extruded through a 200 nm polycarbonate filter (Avanti Polar Lipids, Inc., Alabaster, Ala.) to produce a homogenous suspension of uniform size. The liposome solution was later dialyzed with NANOPURE water to remove any unencapsulated cysteine molecules using a 3.5K MWCO dialysis cassette (G2, Thermo Fisher Scientific, Waltham, Mass.) for at least three hours. The final solution was stored at 4° C. until use. The fabricated liposome can be stable for two weeks at 4° C.

Example 2—Gold Nanoparticle (AuNP) Synthesis

All glassware used for AuNPs synthesis are cleaned in NOCHROMIX solution (Godax Laboratories, Inc., Cabin John, Md.) and then aqua regia (3 parts HCL+1 part $HNO_3$) according to standard lab procedure. The synthesis of citrate-stabilized gold nanoparticle (AuNP) was based on a modification of Turkevich method. (Enustum et al., 1963, J. Am. Chem. Soc. 85(21):3317-3328). Briefly, 100 mL solution of 1 mM $HAuCl_4$ (Sigma-Aldrich, St. Louis, Mo.) was boiled with stirring until bubbles formation and having a uniform temperature. Heating was kept for a further 25 minutes. Then, 10 mL of preheated trisodium citrate (38.8 mM, Sigma-Aldrich, St. Louis, Mo.) was added to the boiling $HAuCl_4$ solution quickly. The solution turned to colorless for a moment, followed by violet to dark ruby red. The solution was heated for a further five minutes before cooling to room temperature. The solution was stored in the dark in a flask covered with foil. The sizes of AuNPs were characterized to be 32±3 nm using transmission electron microscopy (TECHNAI T12, FEI, Hillsboro, Oreg.).

Example 3—Sandwich LAPIA/LCR Assay for IgG Detection

The 96-well polystyrene plated (Sarstedt AG &. Co., Nümbrecht, Germany) were modified with 100 μl of anti-rabbit IgG produced in goat (100 μg/ml, Sigma-Aldrich, St. Louis, Mo.) in carbonate buffer pH 9 at 4° C. overnight. The plate was then washed three times with washing buffer (1×PBS Tween-20, Thermo Fisher Scientific, Waltham, Mass.) before being blocked with blocking buffer (1 mg/ml BSA in PBS buffer) for one hour at room temperature. Subsequently, the plate was washed three times with washing buffer and 100 μl of rabbit IgG (Sigma-Aldrich, St. Louis, Mo.) at different final concentration diluted from a stock solution with 0.5 mg/ml BSA in PBS. After being incubated for two hours, the plate was washed three times with washing buffer, and biotinylated goat anti-rabbit IgG (100 μl, Sigma-Aldrich, St. Louis, Mo.) diluted 1:1000 in blocking buffer was added for 1 h at room temperature. After washing three times, the streptavidin conjugated $PLA_2$ (40 μl of 1:5 dilution in blocking buffer; Sigma-Aldrich, St. Louis, Mo.) was added for one hour at room temperature. Signal Generation in LAPIA/LCR with AuNPs Aggregation.

After washing the plate once with washing buffer, twice with PBS buffer, and once with deionized water, 50 μL of cysteine-encapsulated liposome was added along with 1 μL of $CaCl_2$ (10 mM, Sigma-Aldrich, St. Louis, Mo.). After 5 minutes, 100 μL of AuNP solution (pH 8.5) was added to each well. The absorbance spectra were recorded after 10 minutes using UV-vis photospectrometer (UV-1800, Shimadzu America, Inc., Columbia, Md.). Photographs were taken at five-minute intervals after the addition of AuNPs. Results are shown in FIG. 7.

The aggregation of AuNPs was analyzed by transmission electron microscopy (TECHNAI T12, FEI, Hillsboro, Oreg.) at an acceleration voltage of 120 kV.

Example 4—Sandwich LAPIA Immunoassay for the Detection of Live Pathogens

Three pathogens, *Escherichia coli* O157:H7, *Salmonella typhimurium*, and *Listeria monocytogenes*, were used as models for the PIC-LISA tests with boiled (100° C. in 15 minutes) and live bacteria solutions. The bacteria were diluted to different concentration in physiological saline solution. 96-well polystyrene plates (Sarstedt AG & Co., Nümbrecht, Germany) were modified with 100 μL goat anti-mouse IgG (Fc specific), diluted to concentration of 3 μg/mL in carbonate buffer (100 mM, pH 9.6) for overnight at 4° C. After washing three times with wash buffer, the plates were blocked with blocking buffer (0.5% BSA in 10 mM PBS buffer, pH 7.4) for two hours at room temperature. 100 μL, 1 μg/mL of mouse monoclonal anti-*E. coli* O157:H7, anti-*Salmonella Typhimurium*, and anti-*Listeria monocytogenes* (Abcam plc, Cambridge, Mass.) was added and incubated two hours at room temperature or at 4° C. overnight. After washing the plates three times with wash buffer, each pathogen solution was added to the desired concentration from diluted solution in saline buffer. After being incubated for one hour at 37° C., the plates were washed three times with wash buffer, and 100 μL of goat polyclonal anti-*E. coli* O157 (2 μg/mL), rabbit polyclonal anti-*Salmonella* (4 ug/mL), or rabbit polyclonal anti-*Listeria* (4 ug/mL), diluted in blocking buffer, were added to the plates and incubated for one hour at 37° C. The plates were then washed three times and 100 μL of either biotinylated anti-goat IgG, or anti-rabbit IgG, diluted 1:1000 in blocking buffer, were added and incubated for one hour at 37° C. After washing the plates three time, 100 µL of streptavidin (2 µg/mL in blocking buffer) was added and incubated for 30 minutes at room temperature. Then, the plate was washed twice with wash buffer, twice with 10 mM PBS, pH 7.4 to remove any TWEEN 20 remaining in the plate. The plates were incubated with 50 µL of Lipo-cys-biotin solution for 30 minutes at room temperature. At the last five minutes of incubation, 150 µL of 10 mM PBS buffer, pH 7.4 was added to each well. The plate was then washed twice with 10 mM PBS buffer, pH 7.4 with gentle tapping the plate to remove non-binding liposome vesicles. Color generation was done in a similar manner to IgG assay with optical reading at 655 nm for quantification.

Figure 6:
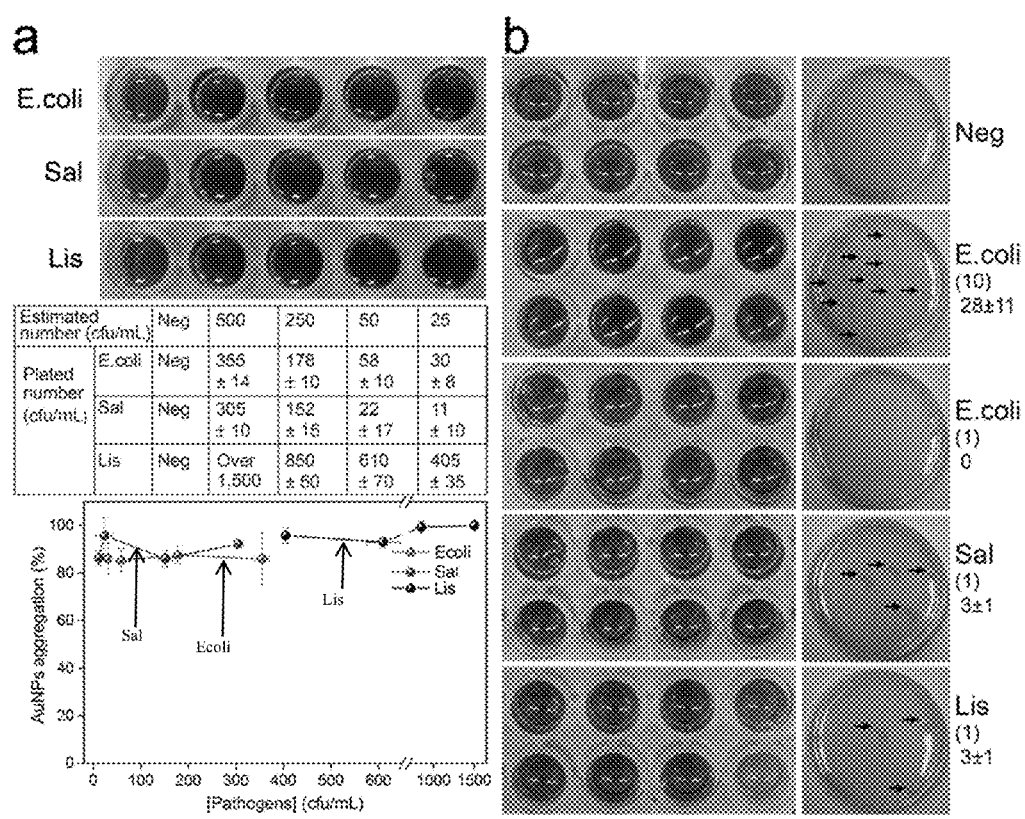
FIG. 6. (A) Naked-eye detection of foodborne bacteria using LAPIA concept. Optical photographs of LAPIA detecting *Escherichia coli* O157:H7, *Salmonella typhimurium*, and *Listeria monocytogenes*, labeled *E. coli*, Sal and Lis, respectively (top). The bacteria were diluted and detected in water at different concentrations. The table represents the estimated and counted number of bacteria using cell plating (middle). The graphic shows all-or-none response for all concentrations with maximum aggregation of AuNPs (absorbance measured at 655 nm) (bottom). (B) LAPIA test detection of foodborne pathogens at single-digit numbers (left) which was confirmed with cell plating (right). At low bacteria numbers (e.g., fewer than four bacteria), only 2-to-3 out of eight microwells showed positive response, indicating the detection of one or two bacteria in each well. The estimated (bracketed) and plated bacteria numbers showed consistent results with the LAPIA test.

Results are shown in FIG. 6.

Example 5—Detection of Foodborne Pathogens in Food Samples

To study the impact of food matrices on the detection of pathogens using LAPIA test, selected food samples were exposed to known concentrations of a specific foodborne bacterium. Briefly, milk and apple juice were used as purchased and were respectively inoculated with *E. coli* and *Salmonella*. Ground beef (25 g) was mixed in 25 mL PBS buffer at pH 7.4, and then the suspension was filtered through polycarbonate membrane (0.2 µm) and the filtered solution inoculated with *Listeria* before use. All food samples were exposed to known concentrations of pathogens, which were later determined by cell plating in 1% diluted PBS-BSA buffer solution, with a volume ratio of 5:5:2 for bacterial suspension, food matrix, and diluted buffer solution respectively. The LAPIA test was performed as described in Example 4.

Figure 8:
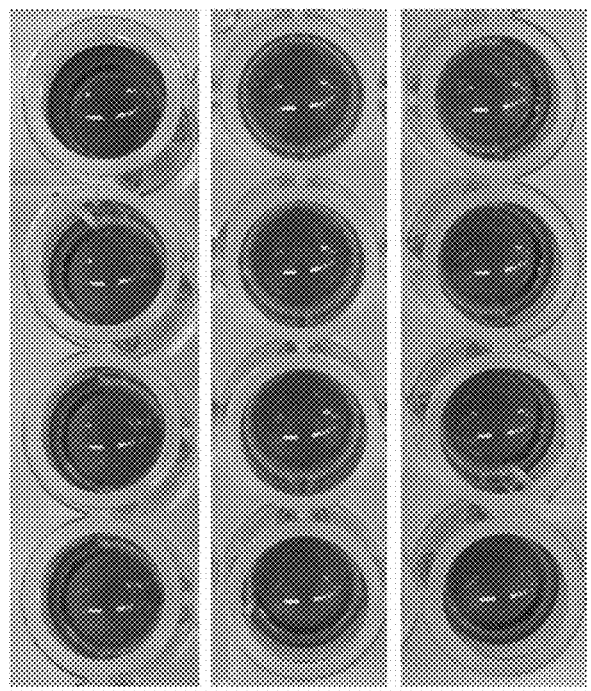
FIG. 8. LAPIA test for detecting *E. coli* in milk, *Salmonella* in apple juice, and *Listeria* in ground beef. The photograph of the assay showed positive reaction for each bacterium (top). The number of bacteria in each test was estimated and confirmed with cell plating (middle). The graphic shows the ratio of AuNPs aggregation based on absorption measurements at 655 nm (bottom).

Results are shown in FIG. 8.

Example 6

$Fe_3O_4$ nanoparticles were synthesized by heating ferric chloride hexahydrate ($FeCl_3.6H_2O$) and ferrous chloride tetrahydrate ($FeCl_2.4H_2O$) for 45 minutes at 80° C. During the heating process, the pH of the solution was adjusted to 10.0 with ammonium chloride, causing the formation of a nanoparticle precipitate. This precipitate was washed with water and acetone and finally dried for later use. These magnetic particles were then functionalized with (3-aminopropyl)triethoxysilane (APTES) in order to provide an active amine group for further conjugation. This reaction was carried out by treating the synthesized $Fe_3O_4$ with APTES and equal parts toluene/methanol for 20 hours at 80° C. For antibody conjugation, the magnetic particles were treated with 1-ethy-3-(3-dimethylaminopropyl)carbodiimide (EDC) for 25 minutes at 4° C. The particles were separated using a magnet. Streptavidin was added and the solution was sonicated in an ultrasonic bath for one hour at 4° C.

UV-visible spectra were taken (at 280 nm) before and after the streptavidin was added to confirm conjugation. The solution was again separated using a magnet and biotinylated antibodies were added to the separated particles for two hours at room temperature with shaking at 60 rpm. Conjugation was again confirmed via UV-visible spectroscopy. Particles were then separated and stored in phosphate buffer solution (pH 7.4) at 4° C.

A non-pathogenic strain of *E. coli* was used (ATCC: 25922) as a model target microbe. 100 µL of the synthesized magnetic particles were mixed with sample solutions at known concentrations for one hour at room temperature with shaking at 60 rpm. After this incubation, the magnetic particles were separated from the solution and were washed one time with a phosphate buffer solution. Next, the particles were mixed with 1% bovine serum albumin for one hour to block any unreacted bonding sites on the surface of the magnetic particles. The particles were again separated and washed. Biotinylated anti-*E. coli* antibodies were then added to the particles for one hour. In the presence of the targeted pathogen, a biomolecular "bridge" including captured pathogen is created, as shown in FIG. 9A-2.

After another washing step, streptavidin was added to the particles for 30 minutes. Finally, after another washing step, biotinylated cysteine-encapsulating liposomes were added to the particles. This solution was washed with phosphate buffer. 500 µL of gold nanoparticles were added along with 50 µL of phosphate buffer containing Tween-20. If the target microbe is present in the system, free cysteine induces the aggregation of gold nanoparticles which yields a distinct red-to-blue color change. If the target microbe is not present in the system, then the antibodies and liposomes are simply washed away and the gold remains red upon addition of Tween-20.

Exemplary Embodiments

Embodiment 1

A method for detecting a target, the method comprising:
providing a capture agent that specifically binds to the target;
contacting a sample that includes the target with the capture agent, thereby allowing the target to bind to the capture agent;
removing unbound sample;
providing a recognition unit that specifically binds to the target and comprises a vesicular compartment that contains a chromogenic trigger;
contacting the recognition unit with the target bound to the capture agent, thereby allowing the recognition unit to specifically bind to the target;
removing unbound recognition units;
contacting a lysis agent with the vesicular compartment, thereby allowing the lysis agent to lyse the vesicular compartment, releasing the chromogenic trigger; and
contacting a composition that comprises a chromogenic reagent with the released chromogenic trigger, thereby allowing the chromogenic trigger to induce the chromogenic reagent to produce a colorimetric signal.

Embodiment 2

A method for detecting a target, the method comprising:
providing a capture agent that specifically binds to the target;
contacting a sample that includes the target with the capture agent, thereby allowing the target to bind to the capture agent;
removing unbound sample;
providing a recognition unit that specifically binds to the target and comprises a primary vesicular compartment that contains an activatable lysis agent;
contacting the recognition unit with the target bound to the capture agent, thereby allowing the recognition unit to specifically bind to the target;
removing unbound recognition units;

contacting the primary vesicular compartment with a activation agent that activates the lysis agent, thereby activating the lysis agent to lyse the primary vesicular compartment and release the lysis agent;

providing a composition comprising secondary vesicular compartments containing a chromogenic trigger;

contacting the secondary vesicular compartments with the lysis agent released from the primary vesicular compartment, thereby allowing the lysis agent to lyse at least a portion of the secondary vesicular compartments, releasing the chromogenic trigger; and contacting a composition that comprises a chromogenic reagent with the released chromogenic trigger, thereby allowing the chromogenic trigger to induce the chromogenic reagent to produce a colorimetric signal.

Embodiment 3

A method for detecting a target, the method comprising:

providing a capture agent that specifically binds to the target;

contacting a sample that includes the target with the capture agent, thereby allowing the target to bind to the capture agent;

removing unbound sample;

providing a recognition unit that specifically binds to the target and comprises a lysis agent;

contacting the recognition unit with the target bound to the capture agent, thereby allowing the recognition unit to specifically bind to the target;

removing unbound recognition units;

providing a composition comprising vesicular compartments containing a chromogenic trigger;

contacting the vesicular compartment composition with the lysis agent, thereby allowing the lysis agent to lyse at least a portion of the vesicular compartments, releasing the chromogenic trigger; and contacting a composition that comprises a chromogenic reagent with the released chromogenic trigger, thereby allowing the chromogenic trigger to induce the chromogenic reagent to produce a colorimetric signal.

Embodiment 4

The method of any preceding Embodiment wherein the capture agent is immobilized to a substrate.

Embodiment 5

The method of any one of Embodiments 1-3 wherein the capture agent is free in solution.

Embodiment 6

The method of any one of Embodiments 1-3 wherein the capture agent is bound to a carrier.

Embodiment 7

The method of Embodiment 6 wherein the carrier comprises a metal, a particle, a vesicular compartment.

Embodiment 8

The method of any preceding Embodiment wherein the capture agent comprises an antibody.

Embodiment 9

The method of any one of Embodiments 1-7 wherein the capture agent comprises an aptamer.

Embodiment 10

A kit for detecting a target, the kit comprising:
a recognition unit comprising:
 a recognition moiety that specifically binds to the target, and
 a signal initiation moiety that comprises:
 a lysis agent,
 a vesicular compartment that contains a chromogenic trigger, or
 a vesicular compartment that contains an activatable lysis agent, or
 a vesicular compartment that includes a compound that can generate a detectable signal; and
a chromogenic reagent.

Embodiment 11

The kit of Embodiment 10 wherein the signal initiation moiety comprises a lysis agent and the kit further includes a composition comprising vesicular compartment that contain a chromogenic trigger.

Embodiment 12

The kit of Embodiment 10 wherein the signal initiation moiety comprises a vesicular compartment that contains a chromogenic trigger and the kit further comprises a lysis agent.

Embodiment 13

The kit of Embodiment 10 wherein the signal initiation moiety comprises a vesicular compartment that contains an activatable lysis agent and the kit further comprises:
 a composition that comprises an activation agent that activates the activatable lysis agent; and
 a composition that comprises vesicular compartments that contain a chromogenic trigger.

Embodiment 14

The kit of Embodiment 10 wherein the compound that can generate a detectable signal comprises an electrogenic compounds that can generate a signal readable by an electrochemical device.

Embodiment 15

The kit of Embodiment 10 wherein the compound that can generate a detectable signal comprises a fluorogenic compound that can generate a fluorescent signal.

Embodiment 16

The kit of Embodiment 10 wherein the compound that can generate a detectable signal comprises an optically active compound that can generate a signal readable by optical spectroscopy.

Embodiment 17

The kit of Embodiment 10 wherein the compound that can generate a detectable signal comprises a chemiluminescent compound that can generate a chemiluminescence readable by a luminometer.

Embodiment 18

The kit of Embodiment 10 wherein at least one kit component is lyophilized or freeze-dried.

Embodiment 19

A method for detecting a target, the method comprising:
providing a capture agent that specifically binds to the target, the capture agent displaceably bound to a lysis agent;
contacting a sample that includes the target with the capture agent, thereby allowing the target to bind to the capture agent and displace the lysis agent;
contacting a composition comprising vesicular compartments containing a chromogenic trigger with the displaced lysis agent, thereby allowing the displaced lysis agent to lyse at least a portion of the vesicular compartments, releasing the chromogenic trigger; and
contacting a composition that comprises a chromogenic reagent with the released chromogenic trigger, thereby allowing the chromogenic trigger to induce the chromogenic reagent to produce a colorimetric signal.

Embodiment 20

The method of Embodiment 19 wherein the capture agent is bound to a carrier.

Embodiment 21

The method of Embodiment 20 wherein the carrier comprises a metal, a particle, a vesicular compartment.

Embodiment 22

The method of Embodiment 21 wherein the carrier comprises the vesicular compartment containing a chromogenic trigger, so that (a) contacting the sample that includes the target with the capture agent and (b) contacting the composition comprising vesicular compartments containing a chromogenic trigger with the displaced lysis agent occur in a single step.

Embodiment 23

The method of Embodiment 19 wherein the capture agent is immobilized to a substrate.

Embodiment 24

The method of Embodiment 19 wherein the capture agent is free in solution.

Embodiment 25

The method of any one of Embodiments 19-24 wherein the capture agent comprises a nucleic acid.

Embodiment 26

The method of Embodiment 25 wherein the nucleic acid comprises an aptamer.

The complete disclosure of all patents, patent applications, and publications, and electronically available material cited herein are incorporated by reference in their entirety. In the event that any inconsistency exists between the disclosure of the present application and the disclosure(s) of any document incorporated herein by reference, the disclosure of the present application shall govern. The foregoing detailed description, examples, and exemplary Embodiments have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method for detecting a target, the method comprising:
providing a capture agent that specifically binds to the target;
contacting a sample that includes the target with the capture agent, thereby allowing the target to bind to the capture agent;
removing unbound sample;
providing a recognition unit that specifically binds to the target, the recognition unit comprising a vesicular compartment that contains a chromogenic trigger;
contacting the recognition unit with the target bound to the capture agent, thereby allowing the recognition unit to specifically bind to the target;
removing unbound recognition units;
contacting a lysis agent with the vesicular compartment, thereby allowing the lysis agent to lyse the vesicular compartment, releasing the chromogenic trigger; and
contacting the chromogenic trigger with a composition that comprises a chromogenic reagent, the chromogenic reagent comprising a reagent that aggregates in the presence of the chromogenic trigger, thereby allowing the chromogenic trigger to induce the chromogenic reagent to aggregate and produce a colorimetric signal.

2. The method of claim 1 wherein the capture agent is immobilized to a substrate.

3. The method of claim 1 wherein the capture agent is free in solution.

4. The method of claim 1 wherein the capture agent is bound to a carrier.

5. The method of claim 1 wherein the capture agent comprises an antibody.

6. The method of claim 1 wherein the capture agent comprises an aptamer.

* * * * *